(12) United States Patent
Giordano et al.

(10) Patent No.: US 9,180,237 B2
(45) Date of Patent: Nov. 10, 2015

(54) PORTABLE HEMODIALYSIS MACHINE AND DISPOSABLE CARTRIDGE

(71) Applicant: ASIT ENGINEERING CORP., Laguna Hills, CA (US)

(72) Inventors: Renato Giordano, Laguna Hills, CA (US); Rodney Corder, Chesterton, IN (US)

( * ) Notice: Subject to any disclaimer, the term of this patent is extended or adjusted under 35 U.S.C. 154(b) by 0 days.

(21) Appl. No.: 14/632,421

(22) Filed: Feb. 26, 2015

(65) Prior Publication Data

US 2015/0238678 A1     Aug. 27, 2015

Related U.S. Application Data

(60) Provisional application No. 61/945,698, filed on Feb. 27, 2014.

(51) Int. Cl.
*A61M 1/14*     (2006.01)
*A61M 1/16*     (2006.01)

(52) U.S. Cl.
CPC ........... *A61M 1/1603* (2014.02); *A61M 1/1621* (2014.02)

(58) Field of Classification Search
USPC ................................................ 604/4.01–6.16
See application file for complete search history.

(56) References Cited

U.S. PATENT DOCUMENTS

| | | |
|---|---|---|
| 4,353,368 A | 10/1982 | Slovak et al. |
| 4,650,587 A | 3/1987 | Polak et al. |
| 4,661,246 A | 4/1987 | Ash |
| 5,336,165 A | 8/1994 | Twardowski |
| 5,484,397 A | 1/1996 | Twardowski |
| 5,858,186 A | 1/1999 | Glass |
| 5,902,476 A | 5/1999 | Twardowski |
| 5,944,684 A | 8/1999 | Roberts et al. |
| 7,241,272 B2 | 7/2007 | Karoor et al. |
| 7,890,341 B2 | 2/2011 | McNally et al. |
| 7,901,376 B2 | 3/2011 | Steck et al. |
| 7,955,290 B2 | 6/2011 | Karoor et al. |
| 7,955,295 B2 | 6/2011 | Lee et al. |
| 8,002,726 B2 | 8/2011 | Karoor et al. |
| 8,066,658 B2 | 11/2011 | Karoor et al. |
| 8,109,893 B2 | 2/2012 | Lande |
| 8,409,444 B2 | 4/2013 | Wong |
| 8,491,517 B2 | 7/2013 | Karoor et al. |
| 8,496,609 B2 | 7/2013 | Childers et al. |
| 8,540,886 B2 | 9/2013 | Hedmann et al. |

(Continued)

*Primary Examiner* — Philip R Wiest
(74) *Attorney, Agent, or Firm* — David G. Duckworth; Russo & Duckworth, LLP

(57) ABSTRACT

A portable hemodialysis system is provided suitable for in home use. The hemodialysis system includes a disposable cartridge and a reused dialysis machine. The disposable cartridge includes a dialyzer, and a dialysate flow path and a blood flow path which flow in opposing directions through the dialyzer. In addition, the disposable cartridge possesses pump actuators (but not pump motors) for pumping dialysate and blood through their respective flow paths. The pump actuators having non-deformable components including a housing having a central cavity forming an internal sidewall, a rotor eccentrically positioned within the cavity having radially aligned slots at the rotor's periphery, and vanes slideably positioned in the slots to slide in and out of the slots so as to seal with the cavity's internal sidewall creating vane chambers that pump blood or dialysate.

6 Claims, 15 Drawing Sheets

(56) References Cited

U.S. PATENT DOCUMENTS

| | | |
|---|---|---|
| 8,647,506 B2 | 2/2014 | Wong |
| 8,685,244 B2 | 4/2014 | Heyes et al. |
| D706,836 S | 6/2014 | Giordano |
| 8,753,515 B2 * | 6/2014 | Curtis .................... A61M 1/16 210/646 |
| 8,777,892 B2 | 7/2014 | Sandford et al. |
| 8,815,088 B2 | 8/2014 | Choi et al. |
| 8,894,600 B2 | 11/2014 | Kelly et al. |
| 8,900,174 B2 | 12/2014 | Childers |
| 8,926,540 B2 | 1/2015 | Lo et al. |
| 2013/0213891 A1 | 8/2013 | Karoor |
| 2014/0001112 A1 | 1/2014 | Karoor et al. |

* cited by examiner

PORTABLE HEMODIALYSIS MACHINE AND DISPOSABLE CARTRIDGE

RELATED APPLICATIONS

The present application is a continuation of U.S. Provisional Patent Application Ser. No. 61/945,698 filed on Feb. 27, 2014. The contents of the aforementioned application are incorporated by reference herein.

BACKGROUND OF THE INVENTION

The present invention relates to an artificial kidney system for use in providing dialysis. More particularly, the present invention is directed to a hemodialysis system which significantly improves hemodialysis therapy so as to provide hemodialysis to a broader base of patients and to decrease the overall cost of hemodialysis.

Applicant(s) hereby incorporate herein by reference any and all patents and published patent applications cited or referred to in this application.

Hemodialysis is a medical procedure that is used to achieve the extracorporeal removal of waste products including creatine, urea, and free water from a patient's blood involving the diffusion of solutes across a semipermeable membrane. Failure to properly remove these waste products can result in renal failure.

During hemodialysis, the patient's blood is removed by an arterial line, treated by a dialysis machine, and returned to the body by a venous line. The dialysis machine includes a dialyzer containing a large number of hollow fibers forming a semipermeable membrane through which the blood is transported. In addition, the dialysis machine utilizes a dialysate liquid, containing the proper amounts of electrolytes and other essential constituents (such as glucose), that is also pumped through the dialyzer.

Typically, dialysate is prepared by mixing water with appropriate proportions of an acid concentrate and a bicarbonate concentrate. Preferably, the acid and the bicarbonate concentrate are separated until the final mixing right before use in the dialyzer as the calcium and magnesium in the acid concentrate will precipitate out when in contact with the high bicarbonate level in the bicarbonate concentrate. The dialysate may also include appropriate levels of sodium, potassium, chloride, and glucose.

The dialysis process across the membrane is achieved by a combination of diffusion and convection. The diffusion entails the migration of molecules by random motion from regions of high concentration to regions of low concentration. Meanwhile, convection entails the movement of solute typically in response to a difference in hydrostatic pressure. The fibers forming the semipermeable membrane separate the blood plasma from the dialysate and provide a large surface area for diffusion to take place which allows waste, including urea, potassium and phosphate, to permeate into the dialysate while preventing the transfer of larger molecules such as blood cells, polypeptides, and certain proteins into the dialysate.

Typically, the dialysate flows in the opposite direction to blood flow in the extracorporeal circuit. The countercurrent flow maintains the concentration gradient across the semipermeable membrane so as to increase the efficiency of the dialysis. In some instances, hemodialysis may provide for fluid removal, also referred to as ultrafiltration. Ultrafiltration is commonly accomplished by lowering the hydrostatic pressure of the dialysate compartment of a dialyzer, thus allowing water containing dissolved solutes including electrolytes and other permeable substances to move across the membrane from the blood plasma to the dialysate. In rarer circumstances, fluid in the dialysate flow path portion of the dialyzer is higher than the blood flow portion, causing fluid to move from the dialysis flow path to the blood flow path. This is commonly referred to as reverse ultrafiltration. Since ultrafiltration and reverse ultrafiltration can increase the risks to a patient, ultrafiltration and reverse ultrafiltration are typically conducted only while supervised by highly trained medical personnel.

Unfortunately, hemodialysis suffers from numerous drawbacks. An arteriovenous fistula is the most commonly recognized access point. To create a fistula, a doctor joins an artery and a vein together. Since this bypasses the patient's capillaries, blood flows rapidly. For each dialysis session, the fistula must be punctured with large needles to deliver blood into, and return blood from the dialyzer. Typically, this procedure is done three times a week and for 3-4 hours per each treatment. To a lesser extent, patients conduct hemodialysis at home. Home dialysis is typically done for two hours, six days a week. Home hemodialysis is considered less stressful and is considered more simplistic as typically conducted with catheters. However, home hemodialysis requires more frequent treatment.

Home hemodialysis suffers from still additional disadvantages. Current home dialysis systems are big, complicated, intimidating and difficult to operate. The equipment requires significant training. Home hemodialysis systems are currently too large so as to be portable, thereby preventing hemodialysis patients from traveling. Home hemodialysis systems are expensive and require a high initial monetary investment, particularly compared to in-center hemodialysis where patients are not required to pay for the machinery. Present home hemodialysis systems do not adequately provide for the reuse of supplies, making home hemodialysis economically less feasible to medical suppliers. Because of the above mentioned disadvantages, very few motivated patients undertake the drudgery of home hemodialysis.

Currently, most hemodialysis systems employ peristaltic roller pumps which engage flexible tubing to push fluid through a dialysis flow path or blood flow path. These roller pumps are expensive and inefficient. Also troubling, roller pumps for use in hemodialysis can cause damage to blood platelets and introduces the risk of coagulation.

Accordingly, there is a significant need for a hemodialysis system that is transportable, light weight, easy to use, patient friendly and thus capable of in-home use.

Moreover, it would be desirable to provide a home hemodialysis system that possessed no single point of failure in the pumps, motors, tubes, or electronics which would endanger a patient.

Furthermore, it would desirable to provide a hemodialysis system that employed pumps that did not squeeze blood in in the blood flow path and did not incorporate flexible materials such as employed with peristaltic roller pumps.

In still an additional aspect, it would desirable to provide a hemodialysis system wherein pump components that came in contact with blood or dialysate could be disposed of after a single patient treatment, but that the pump motor could be reused.

Aspects of the present invention fulfill these needs and provide further related advantages as described in the following summary.

SUMMARY OF THE INVENTION

According to a first aspect of the invention, a hemodialysis system is provided including an arterial blood line for connecting to a patient's artery for collecting blood from a patient, a venous blood line for connecting to a patient's vein for returning blood to a patient, a reusable dialysis machine and a disposable cartridge. In a second aspect of the invention, the present invention provides for a cartridge for use in a hemodialysis machine.

The arterial blood line and venous blood line may be typical constructions known to those skilled in the art. For example, the arterial blood line may be traditional flexible hollow tubing connected to a needle for collecting blood from a patient's artery. Similarly, the venous blood line may be a traditional flexible tube and needle for returning blood to a patient's vein. Various constructions and surgical procedures may be employed to gain access to a patient's blood including an intravenous catheter, an arteriovenous fistula, or a synthetic graft.

The disposable cartridge is intended for a single patient treatment and not reused. The disposable cartridge includes a dialyzer of a construction and design known to those skilled in the art. Suitable dialyzers can be obtained from Fresenius Medical Care, Baxter International, Inc., and Nipro Medical Corporation. Preferably, the dialyzer includes a large number of hollow fibers which form a semipermeable membrane.

The disposable cartridge includes a blood flow path and a dialysate flow path. The blood flow path transports blood in a closed loop system by connecting to the arterial blood line and venous blood line for transporting blood from a patient to the dialyzer and back to the patient. Meanwhile, the dialysate flow path transports dialysate in a closed loop system from a reservoir to the dialyzer and back to the reservoir. Both the blood flow path and the dialysate flow path pass through the dialyzer, but are separated by the dialyzer's semipermeable membrane.

Preferably, the cartridge includes three pump actuators. For purposes herein, the term "pump" is meant to refer to both the actuator which uses suction or pressure to move a fluid, and the motor for mechanically moving the actuator. Suitable pump actuators may include an impeller, piston, diaphragm, the lobes of a lobe pump, screws of a screw pump, rollers or linear moving fingers of a peristaltic pump, or any other mechanical construction for moving fluid as can be determined by those skilled in the art. Meanwhile, the motor is the electromechanical apparatus for moving the actuator. The motor may be connected to the pump actuator by shafts or the like. In a preferred embodiment, the disposable cartridge's pump actuators are sliding vane rotary pump constructions including vanes slidably mounted to a rotor which rotates within a housing's central cavity. The rotor is circular and rotates within the larger substantially circular cavity. The center of the rotor is offset relative to the center of the cavity causing eccentricity. The vanes are allowed to slide in and out of the rotor so as to seal with the cavity's internal side wall creating vane chambers that pump fluid. As explained in greater detail below, preferably the disposable cartridge does not include pump motors.

The first and second pump actuators are connected to the dialysate flow path for pumping dialysate through the dialysate flow path from a reservoir to the dialyzer and back to the reservoir. Preferably, a first pump actuator is connected to the dialysate flow path "upflow", (meaning prior in the flow path) from the dialyzer while the second pump actuator is connected to the dialysate flow path "downflow" (meaning subsequent in the flow path) from the dialyzer. Meanwhile, the disposable cartridge's third pump actuator is connected to the blood flow path. The third pump actuator pumps blood from a patient through the arterial blood line, through the dialyzer, and through the venous blood line for return to a patient. It is preferred that the third pump actuator be connected to the blood flow path upflow from the dialyzer. The disposable cartridge may contain more or less than three pump actuators. For example, the dialysate may be pumped through the dialyzer utilizing only a single pump actuator. However, it is preferred that the disposable cartridge contain two pump actuators including a first pump actuator upflow from the dialyzer and a second pump actuator downflow from the dialyzer.

The disposable cartridge also contains a filter connected to the dialysate flow path for removing toxins which have permeated from the blood plasma through the semipermeable membrane into the dialysate. Preferably, the filter is connected to the dialysate flow path downflow from the dialyzer so as to remove toxins transferred by the dialyzer into the dialysate prior to the dialysate being transported to the reservoir. Filter materials for use with the cartridge are well known to those skilled in the art. For example, suitable materials include resin beds including zirconium based resins. Preferably, the filter has a housing containing layers of zirconium oxide, zirconium phosphate and carbon. Acceptable materials are described in U.S. Pat. No. 8,647,506 and U.S. Patent Application Publication No. 2014/0001112. Other acceptable filter materials can be developed and utilized by those skilled in the art without undue experimentation. Preferably, the filter housing includes a vapor membrane capable of releasing gases including ammonia, but not liquids and particularly not the dialysate liquid flowing through the filter.

Preferably, the disposable cartridge contains sensors for monitoring hemodialysis. To this end, preferably the cartridge has a flow sensor connected to the dialysate flow path for detecting fluid flow (volumetric and/or velocity) within the dialysate flow path. In addition, it is preferred that the disposable cartridge contain one or more pressure sensors for detecting the pressure within the dialysate flow path. Preferably, the disposable cartridge also possesses one or more sensors for measuring the pressure and/or fluid flow within the blood flow path. In a preferred embodiment, the cassette possesses four pressure sensors including a first pressure sensor to measure the pressure of the dialysate flow upflow of the dialyzer, a second pressure sensor to measure the pressure of the dialysate flow downflow of the dialyzer, a third pressure sensor to measure the pressure of the blood flow upflow of the dialyzer, and fourth pressure sensor to measure the pressure of the blood flow downflow of the dialyzer. Furthermore, the preferred cassette possesses four flow sensors including a first flow sensor to measure the flow rate of the dialysate flow upflow of the dialyzer, a second flow sensor to measure the flow rate of the dialysate flow downflow of the dialyzer, a third flow sensor to measure the flow rate of the blood flow upflow of the dialyzer, and fourth flow sensor to measure the flow rate of the blood flow downflow of the dialyzer. The pressure and flow rate sensors may be separate components, or pressure and flow rate measurements may made by a single sensor. For example, in a preferred embodiment, the dialysate flow path possesses two pressure sensors for measuring only pressure and two sensors for measuring only flow rate resulting in four sensors monitoring the pressure or flow rate of the dialysate in the dialysate flow path. However, the preferred disposable cartridge includes only two sensors connected to the blood flow path wherein each sensor is capable of measuring both pressure and flow rate. To transfer measurements produced by the flow sensors and pressure sensors, preferably the disposable cartridge possesses externally mounted electrical terminals which are electrically connected to the flow sensors and pressure sensors.

It is preferred that the disposable cartridge be made of a durable, but high strength plastic such as high grade polycarbonate or acrylic. Polycarbonate and/or acrylic are considered advantageous because of their high reflection index capability, for their extreme high electrical resistance, and good dielectric constants. Preferably the cartridge's blood flow path and dialysate flow path are conduits formed within the cartridge's plastic housing. Moreover, it is preferred that the disposable cartridge be tubeless, meaning that there are no flexible tubes accessible to a patient or clinician within the entire hemodialysis system other than the arterial blood line and venous blood line. Specifically, it is preferred that the disposable cartridge housing and pump actuators be made of a hard plastic and do not employ any flexible tubing, such as employed with a peristaltic pump.

In addition to the disposable cartridge, the hemodialysis system includes a reused "dialysis machine" which mates to the disposable cartridge for connecting to and controlling the disposable cartridge's pump actuators and for monitoring the disposable cartridge's sensors. To this end, the preferred dialysis machine includes three pump motors for engaging and operating the cartridge's three pump actuators. More specifically, the dialysis machine includes first and second pump motors for engaging and operating the first and second pump actuators which are connected to the dialysate flow path. The dialysis machine's third pump motor engages and operates the cartridge's third pump actuator connected to the blood flow path for controlling the pumping of blood through the cartridge's blood flow path. Advantageously, preferably the pump motors and pump actuators are easily engagable and disengagable from one another by merely manually pressing the pump actuators against the pump motors without utilizing tools, or causing damage to either the dialysis machine or disposable cartridge. The pump motors and pump actuators can be mechanically connected utilizing various constructions known to those skilled in the art. For example, the pump motors or pump actuators may include keyed shafts positioned to project into and engage keyed receptacles within the corresponding pump actuators or pump motors. However, in a preferred embodiment the pump motors and pump actuators are connected by a plurality of magnets wherein the pump motors possess a plurality of magnets positioned to engage magnets of opposite polarity within the pump actuators.

Preferably, the dialysis machine contains a reservoir for storing a dialysate solution. When the dialysis machine has mated to a disposable cartridge, the reservoir connects to the cartridge's dialysate flow path to form a closed loop system for transporting a dialysate from the reservoir to the cartridge's dialyzer and back to the reservoir. The reservoir may be of any size as required by clinicians to perform an appropriate hemodialysis treatment. However, it is preferred that the reservoir be sufficiently small so as to enable the dialysis machine to be easily portable.

The dialysis machine preferably possesses a heater thermally connected to the reservoir for heating fluids stored within the reservoir. The heater is preferably activated by electricity and includes a resistor which produces heat with the passage of electrical current.

To monitor proper operation of the hemodialysis system, the dialysis machine possesses various sensors. The dialysis machine includes a temperature sensor for measuring the temperature of the fluid within the reservoir. In addition, the dialysis machine possesses a level sensor for detecting the level of fluid in the reservoir. Furthermore, it is preferred that the dialysis machine include a blood leak detector which monitors the flow of dialysate through the dialysate flow path and detects whether blood has inappropriately diffused through the dialyzer's semipermeable membrane into the dialysate flow path.

The dialysis machine preferably includes additional sensors including an ammonia sensor positioned adjacent to the disposable cartridge's vapor membrane so as to sense whether ammonia is forming within the cartridge's filter, a venous blood line pressure sensor for detecting the pressure in the venous blood line, and a bubble sensor connected to the venous blood line for detecting whether gaseous bubbles have formed in the venous blood line. The dialysis machine may also contain a pinch valve connected to the venous blood line for selectively permitting or obstructing the flow of blood through the venous blood line. The pinch valve is provided so as to pinch the venous blood line and thereby prevent the flow of blood back to the patient in the event that any of the sensors have detected an unsafe condition.

The dialysis machine possesses a processor containing the dedicated electronics for controlling the hemodialysis system. The processor contains power management circuitry connected to the pump motors, dialysis machine sensors, and pinch valve for controlling proper operation of the hemodialysis system. In addition, the dialysis machine possesses electrical terminals positioned to engage and electrically connect to the disposable cartridge's electrical terminals so as to connect the cartridge's flow sensors and pressure sensors with the processor so that the processor can also monitor the disposable cartridge sensors as well. The processor monitors each of the various sensors to ensure that hemodialysis treatment is proceeding in accordance with a preprogrammed procedure input by medical personnel into the user interface.

The dialysis machine and disposable cartridge provide a hemodialysis system that is transportable, light weight, easy to use, patient friendly and capable of in-home use.

Advantageously, the disposable cartridge and blood lines are sterilized prior to presentation to a patient, and disposed of after hemodialysis treatment. Because the blood lines connect directly to the disposable cartridge and not to a reused machine, all components, including the non-deformable pump components, that are susceptible to contamination are disposed of after each treatment and replaced prior subsequent treatments. However, the pump motors can be reused in subsequent treatments.

Also, advantageously, the hemodialysis system does not utilize any flexible tubing other than the arterial blood line and venous blood line so as to reduce areas of potential danger to a patient.

Still an additional advantage is that the hemodialysis system employs pumps that do not squeeze blood in the blood flow path.

In addition, the hemodialysis system provides an extraordinary amount of control and monitoring not previously provided by hemodialysis systems so as to provide enhanced patient safety.

Other features and advantages of the present invention will be appreciated by those skilled in the art upon reading the detailed description which follows with reference to the drawings.

DETAILED DESCRIPTION OF THE PREFERRED EMBODIMENTS

Figure 1:
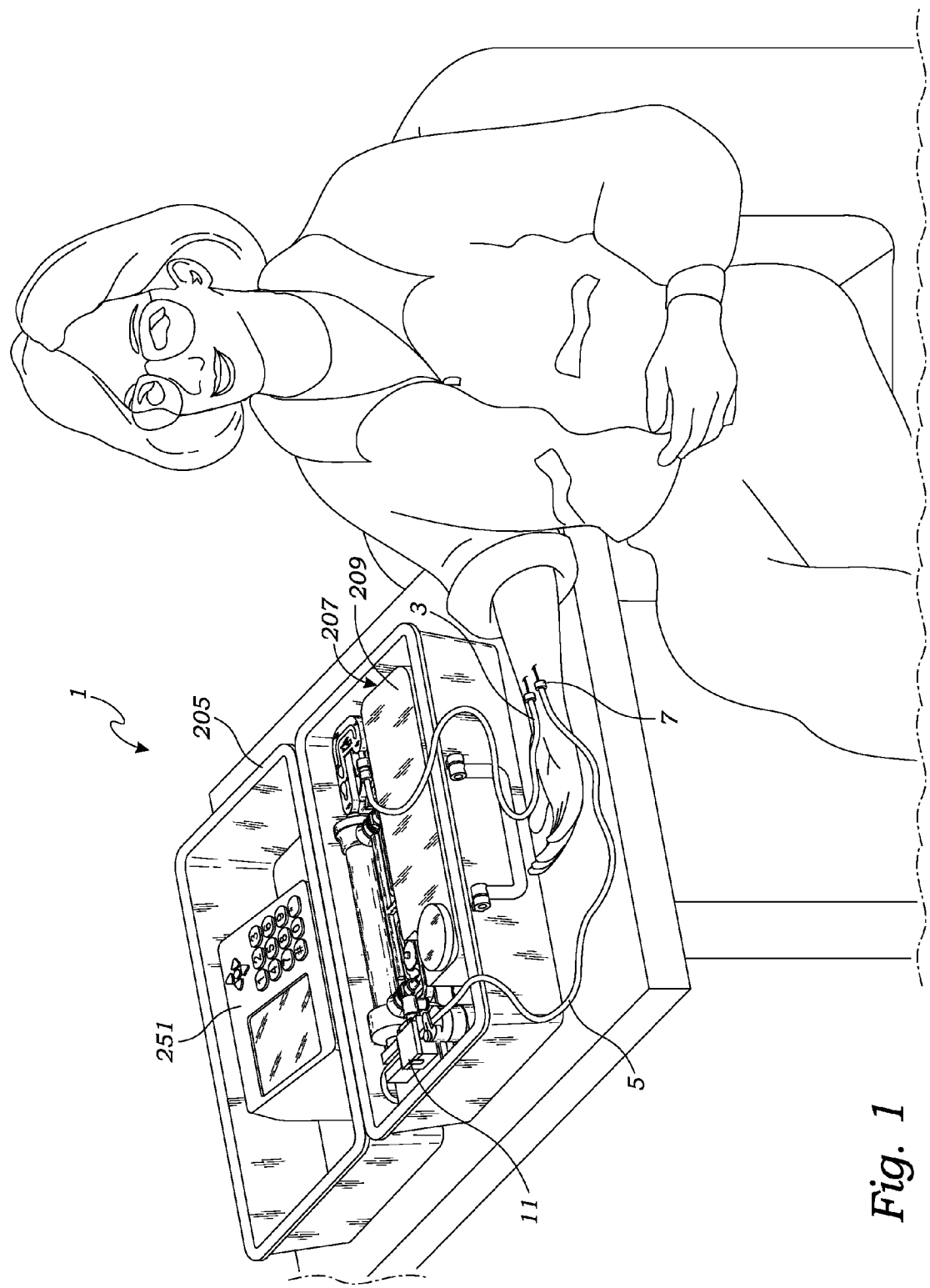
FIG. 1 is a perspective view of the hemodialysis system illustrated in use treating a patient, in accordance with at least one embodiment.

While the present invention is susceptible of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

With reference to FIGS. 1-15, the hemodialysis system 1 of the present invention includes a reused dialysis machine 201, a disposable cartridge 11, an arterial blood line 3 including a needle 7 for connecting to a patient's artery, and a venous blood line 5 including a needle 7 for connecting to a patient's vein. With reference particularly to FIGS. 1-5 and 15, the disposable cartridge 11 includes a housing 13 having conduits 17 providing a blood flow path 15 and conduits 21 providing a dialysis flow path 19. Preferably the cartridge's blood flow path and dialysate flow path are conduits with an approximately 0.156 inch (3-5 millimeters) inside diameter. The disposable cartridge 11 may be a single piece construction. However, preferably and as described herein, the disposable cartridge can be disassembled into multiple pieces such as to allow disengagement of a dialyzer 25 and filter 79, but the multiple pieces can be assembled together to form a disposable cartridge 11. Preferably, the cartridge's housing is made from Federal Drug Administration approved materials. The presently preferred material for the cartridge's housing is polycarbonate plastic.

The disposable cartridge's blood flow path 15 connects at one end to the arterial blood line 3 and at the other end to the venous blood line 5. Both the blood flow path 15 and dialysate flow path 19 travel through a dialyzer 25 to transport their respective fluids through closed loop systems wherein the dialysate flow path is isolated from the blood flow path by a semipermeable membrane (not shown). Preferably, the dialysate flows in the opposite direction to blood flow within the dialyzer 25 which possesses an inlet 31 for receiving dialysate, an outlet 33 for expelling dialysate, an inlet 27 for receiving blood from a patient, and an outlet 29 for returning blood to a patient.

Figure 3:
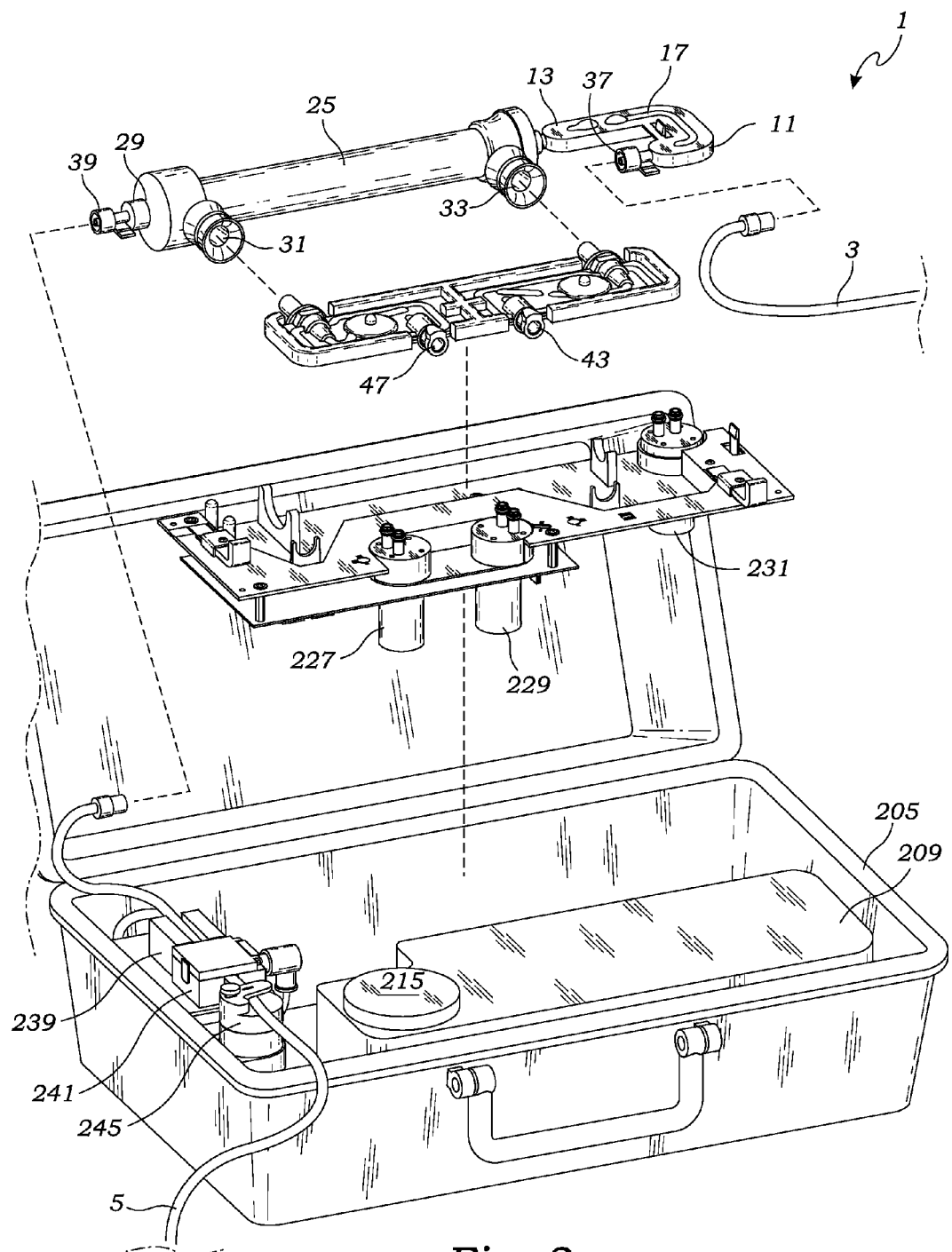
FIG. 3 is an additional exploded perspective view of the hemodialysis system, in accordance with at least one embodiment.
Figure 4:
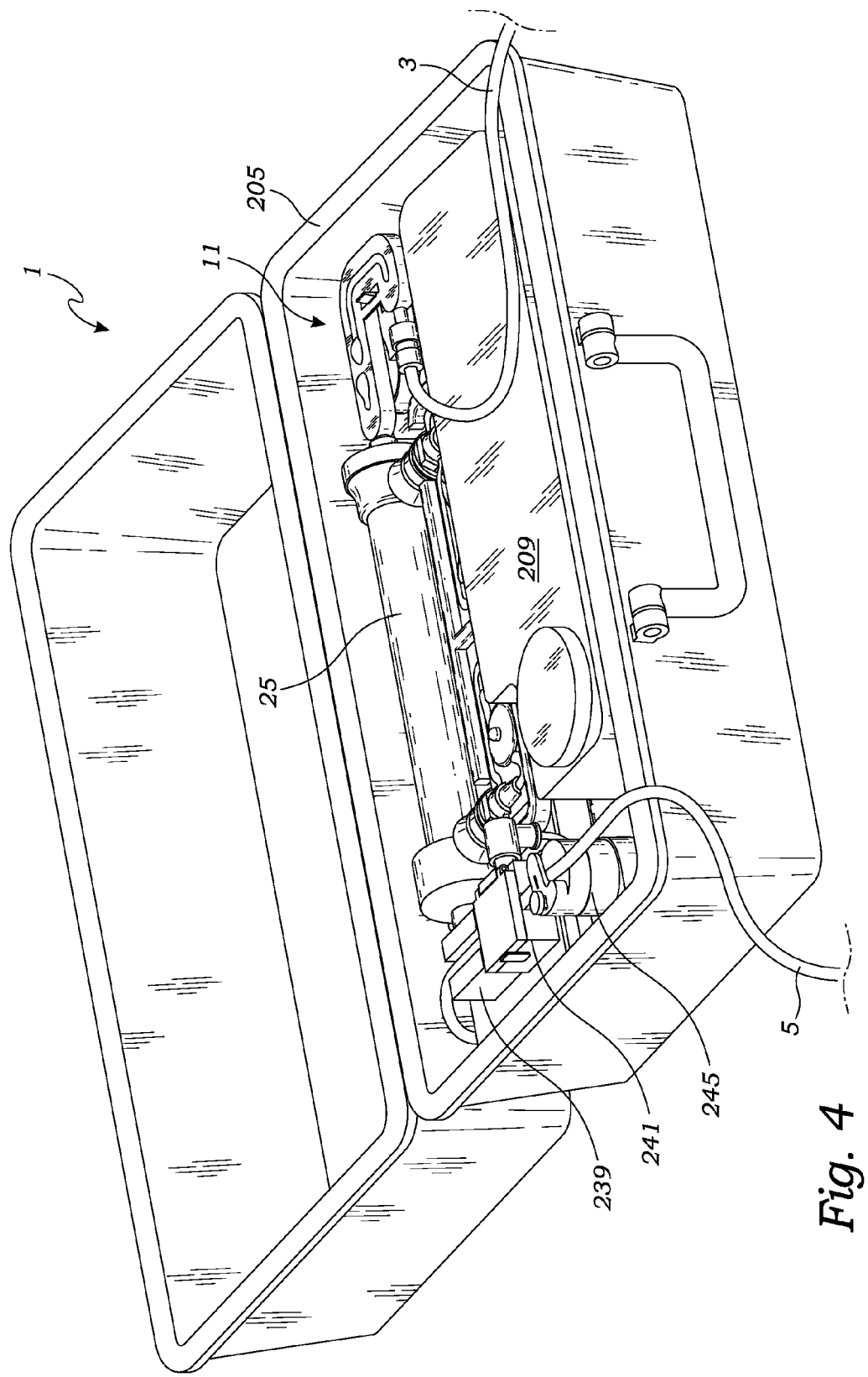
FIG. 4 is a perspective view of the hemodialysis system, in accordance with at least one embodiment.
Figure 9:
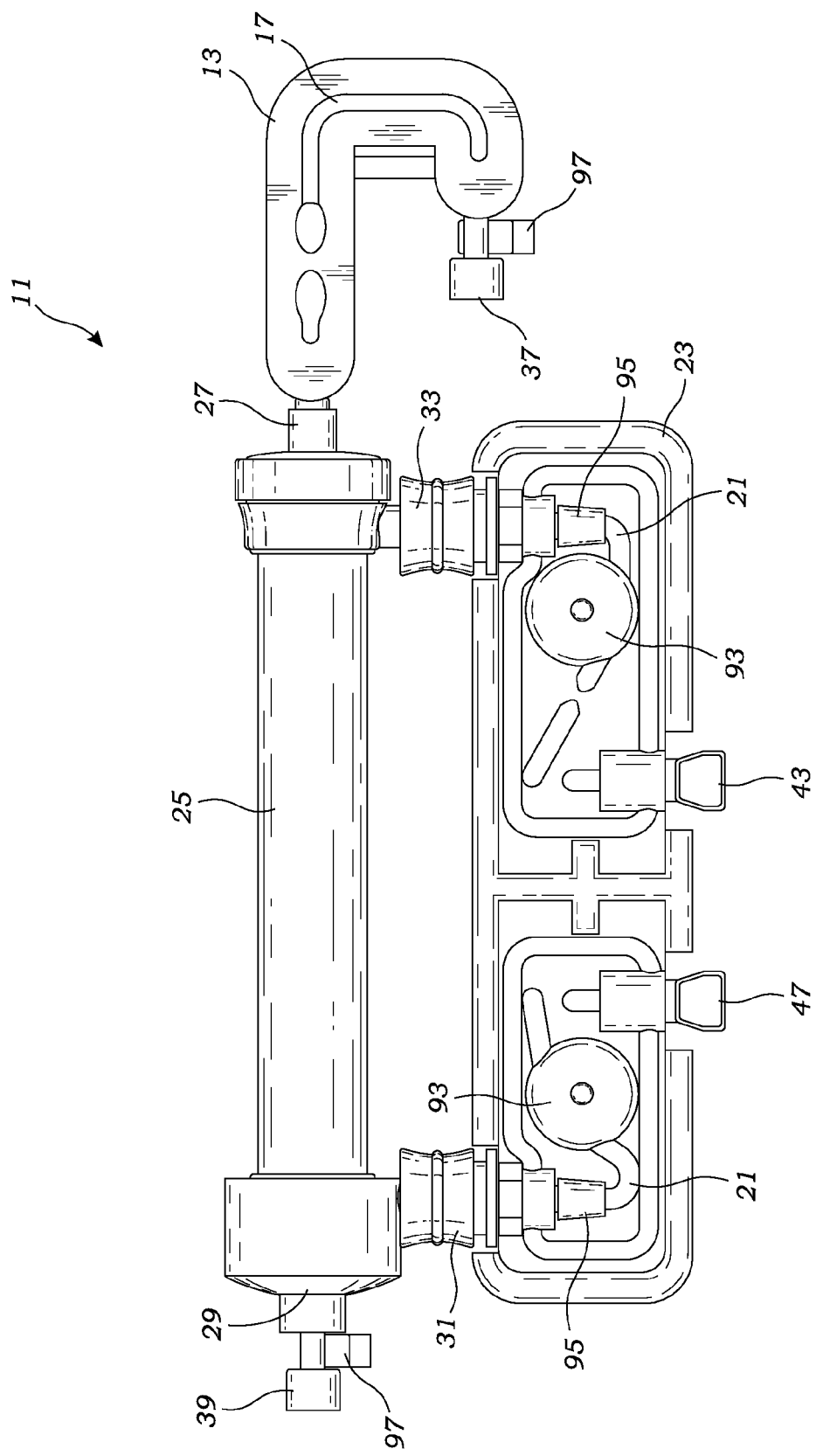
FIG. 9 is a top plan view of the hemodialysis system's disposable cartridge, in accordance with at least one embodiment.
Figure 10:
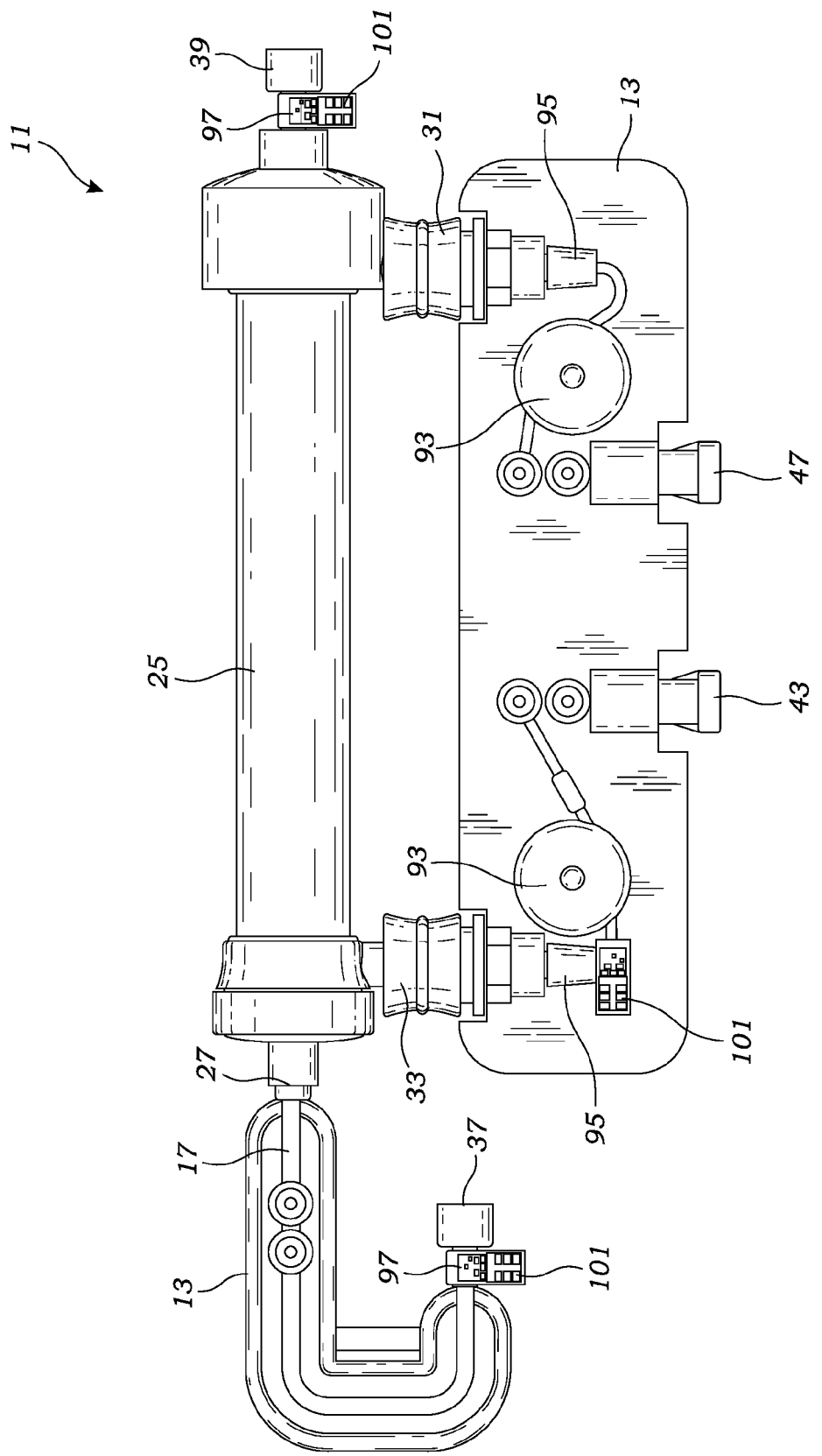
FIG. 10 is a bottom plan view of the hemodialysis system's disposable cartridge, in accordance with at least one embodiment.

More particularly, and as illustrated in FIGS. 1, 3 and 9, the disposable cartridge's housing 13 includes a coupling 37 for connecting the dialyzer's inlet 27 to the arterial blood line 3, and a coupling 39 for connecting the dialyzer's blood outlet 29 to the venous blood line 5. In addition, the disposable cartridge's housing 13 includes a cassette section 23 including conduits 21 for transporting dialysate back and forth from a reservoir 209. To this end, the cassette 23 connects to the dialyzer's inlet 31 and outlet 33 through couplings 47 and 43. Dialysate is received into the cassette 23 through the cassette's coupling 47. Thereafter, the dialysate travels through dialysate flow path 19 (within conduits 21) until entering the dialyzer 25 at the dialyzer's inlet 31. The dialysate then exits the dialyzer 25 at the dialyzer's outlet 33, and continues to travel through the dialysate flow path 19 through conduits 21 until exiting the cassette 23 at coupling 43.

Preferably, the cartridge's cassette 23 possesses two pump actuators 51 and 53. A first pump actuator 51 is positioned upflow of the dialyzer 25 to pump dialysate through the dialysate flow path 19 to the dialyzer 25. The second pump actuator 53 is positioned almost immediately downflow of the dialyzer 25 for pumping dialysate from the dialyzer 25. By independently controlling the operation of the first pump actuator 51 relative to the second pump actuator 53 allows one to increase or decrease the pressure of the dialysate fluid within the dialyzer 25. Preferably the disposable cartridge's housing 13 includes a third pump actuator 55 which is positioned within the housing's coupling 37 which connects to the arterial blood line 3. This third pump actuator 55 pumps blood through the blood flow path 15, and is preferably positioned upflow of the dialyzer 25.

Figure 2:
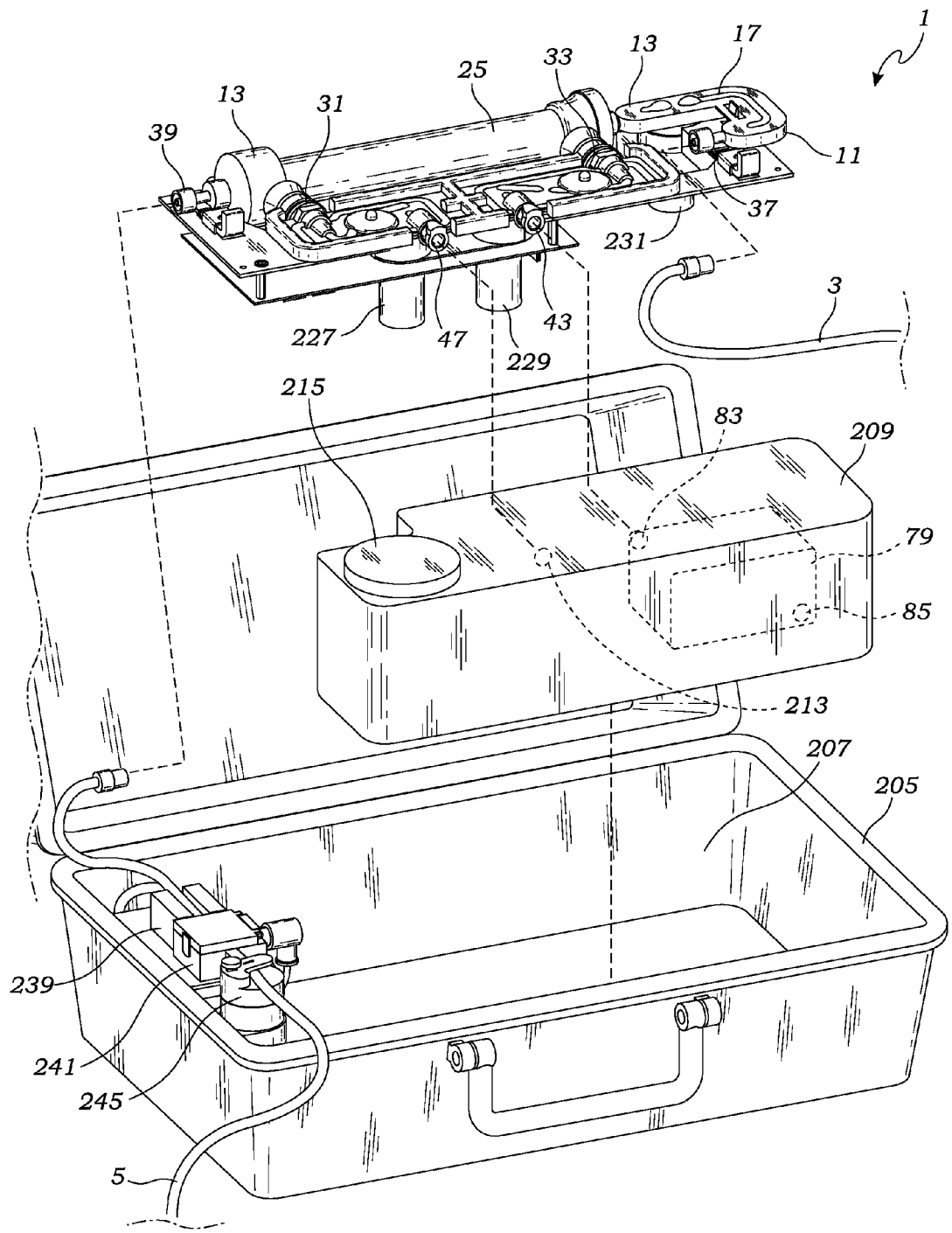
FIG. 2 is an exploded perspective view illustrating the hemodialysis system, in accordance with at least one embodiment.
Figure 7:
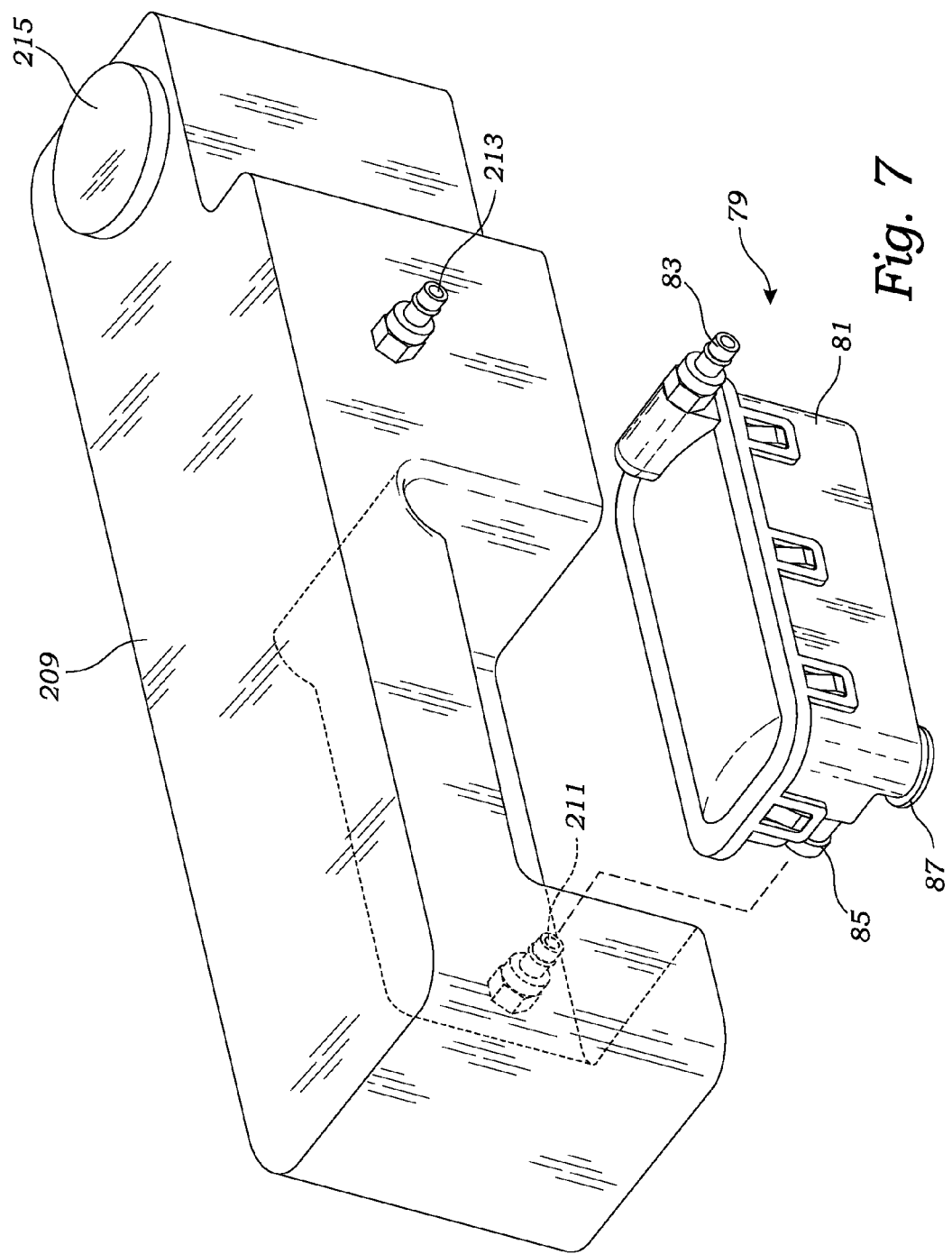
FIG. 7 is an exploded perspective view illustrating the reservoir and filter for use with the hemodialysis system, in accordance with at least one embodiment.
Figure 8:
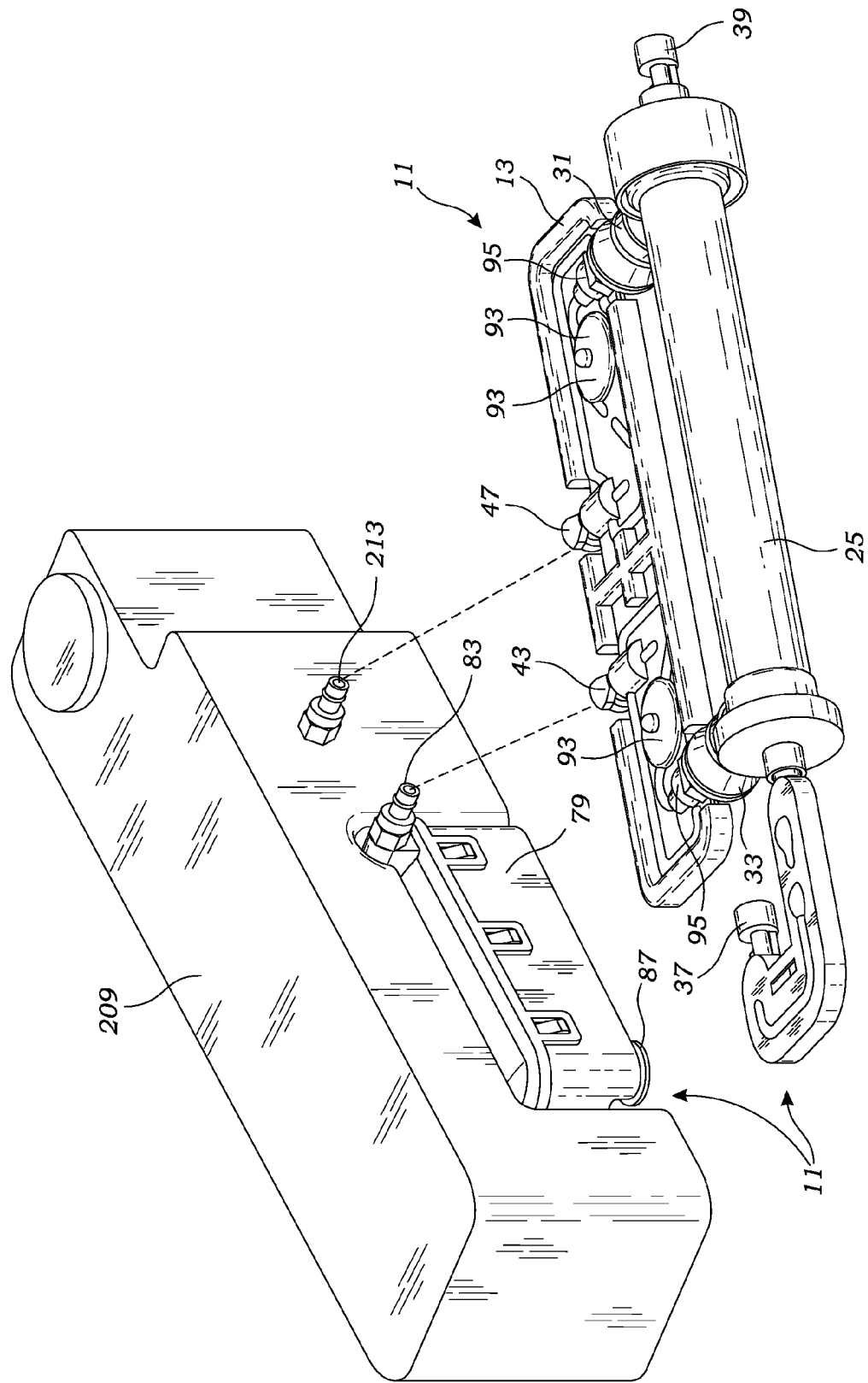
FIG. 8 is a perspective view illustrating the hemodialysis system's disposable cartridge including filter as it connects to the hemodialysis system's reservoir, in accordance with at least one embodiment.

As best illustrated in FIGS. 2, 7 and 8, the disposable cartridge 11 includes a filter 79. The filter 79 includes a housing 81 for encapsulating filter materials for removing toxins from the dialysate liquid. The filter material may be of a composition and construction known or as can be determined by those skilled in the art for removing the various wastes, primarily urea and creatine, from blood. The filter 71 includes an inlet 83 and an outlet 85. The filter's inlet 83 connects to the cassette's coupling 43, and the filter's outlet 85 connects to a reservoir's inlet 211, described in greater detail below. In a preferred embodiment, the filter's housing 81 includes a vapor membrane 87 illustrated in FIGS. 7 and 8.

The vapor membrane 87 is a semipermeable membrane capable of releasing gases including ammonia, but not liquids and particularly not the dialysate liquid, flowing through the filter 79.

As discussed in detail below, the disposable cartridge 11 possesses various sensors for monitoring the dialysis occurring within the dialyzer 25. As illustrated in FIGS. 5-10, the preferred disposable cartridge 11 includes two pairs of flow sensors 93 and pressure sensors 95 in the cassette for measuring the fluid flow and pressure of the dialysate in the dialysate flow path 19. Preferably, the cassette flow sensors 93 are positioned upflow and downflow, respectively, of the dialyzer 25. In a preferred embodiment, each flow sensor 93 includes a circular chamber 91 in the dialysate flow path and rotatable spoked wheel (not shown) within the chamber 91 which is rotated by the flow of dialysate. Preferably, the wheel spokes includes two magnets of opposite polarity which reveal the wheel's rotational position and rotational velocity which is used to determine fluid flow. Preferably, the cassette pressure sensors 95 for measuring dialysate pressure are also positioned upflow and downflow, respectively, of the dialyzer 25 for measuring the pressure of the dialysate prior to the dialysate entering the dialyzer 25 and subsequent to the dialysate leaving the dialyzer 25. The cassette's pressure and flow sensors may be Federal Drug Administration approved sensors as can be selected by those skilled in the art.

Preferably, the disposable cartridge possesses still additional sensors 97 for measuring the pressure and fluid flow of the blood passing through the blood flow path 15 both immediately after the blood is received from a patient, and prior to returning the blood to a patient. In a preferred embodiment, both the pressure and fluid flow measurements of the blood are made by a single sensor. As best illustrated in FIGS. 5, 9, 10, 13 and 15, the preferred cartridge 11 includes a first pressure/fluid sensor 97 within coupling 37 for measuring the pressure and fluid flow of the blood as it is received by the arterial blood line 3 prior to the blood entering the dialyzer 25. In addition, preferably the cartridge possesses a second pressure/fluid sensor 97 within the coupling 39 for measuring the pressure and fluid flow of the blood prior to the blood being returned to the patient through the venous blood line 5. To transfer measurements produced by the cassette flow sensors and pressure sensors, the disposable cartridge 11 possesses electrical terminals 101.

The hemodialysis system's dialysis machine 201 is best illustrated in FIGS. 1-5. Preferably, the dialysis machine 201 possesses a case 205 having a cavity 207 for encapsulating and protecting the various components of the dialysis machine 201 and disposable cartridge 11. Preferably, the case 205 is of a size suitable for travel in an overhead bin of a commercial airliner. The dialysis machine 201 possesses a reservoir 209 for storing the dialysate during the hemodialysis procedure. A preferred reservoir stores 1 gallon (3.785 liters) of dialysate which can be introduced into the reservoir through the reservoir's removable cap 215. In addition, the reservoir 209 includes an inlet 211 and an outlet 213. As best illustrated in FIG. 7, the reservoir's inlet 211 connects to the disposable cartridge's filter's outlet 85. Meanwhile, the reservoir's outlet 213 connects to the disposable cartridge's connector 47. Preferably the dialysis machine possesses a heater 221 (illustrated in FIG. 15) which is thermally coupled to the reservoir 209 for heating and maintaining the temperature of the dialysate at a desired temperature.

Figure 5:
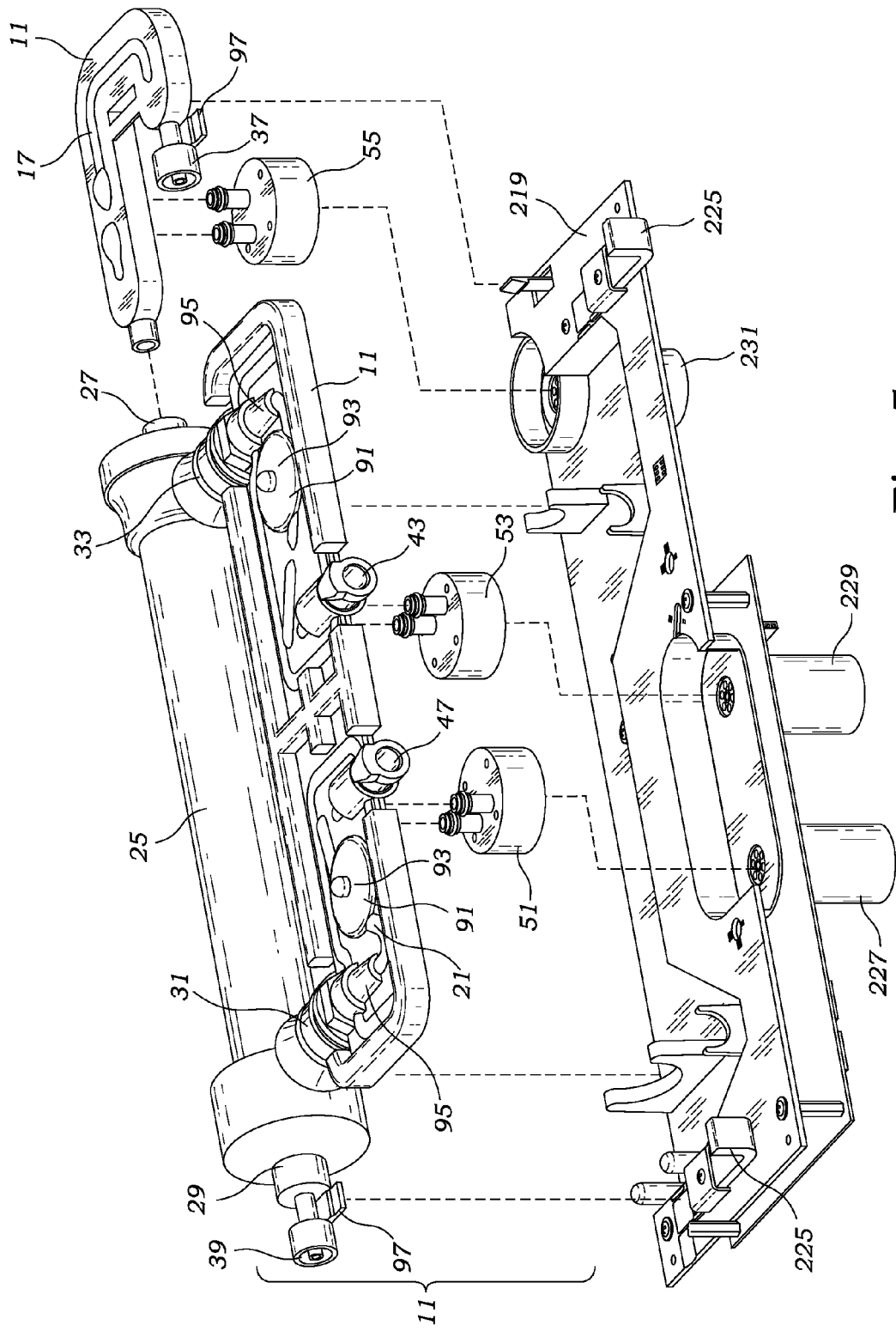
FIG. 5 is an exploded perspective view of the hemodialysis system's disposable cartridge above the dialysis machine's tray, in accordance with at least one embodiment.
Figure 6:
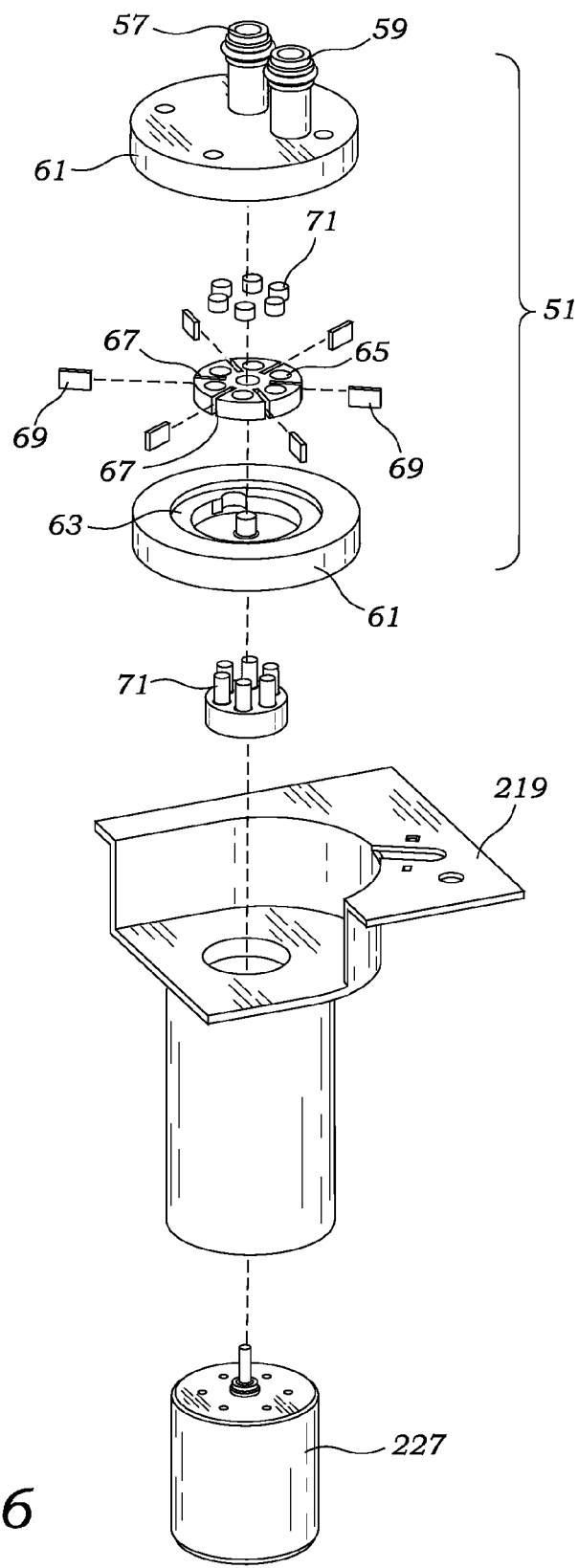
FIG. 6 is an exploded perspective view illustrating a preferred pump, including pump actuator and pump motor, for use with the hemodialysis system, in accordance with at least one embodiment.
Figure 11:
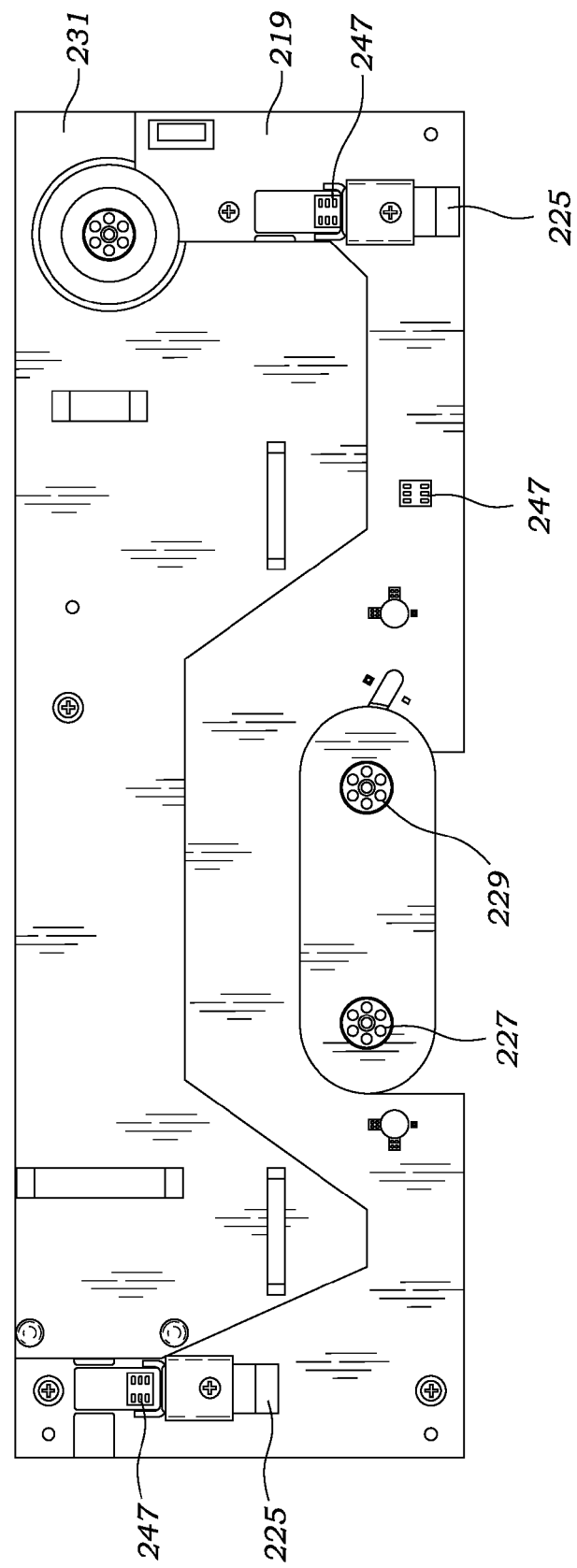
FIG. 11 is a top plan view illustrating the dialysis machine's tray for receiving the disposable cartridge, in accordance with at least one embodiment.

Preferably the dialysis machine 201 includes a tray 219 for supporting and mating to the disposable cartridge's housing 13, dialyzer 25, arterial line coupling 37, and venous line coupling 39. The tray 219 may include latches 225 for locking the disposable cartridge 11 in engagement with the dialysis machine 201. In the preferred embodiment, the tray 219 also includes three pump motors (227, 229 and 231) for coupling to the disposable cartridge's three pump actuators (51, 53 and 55). With reference to FIGS. 5, 6 and 11, the dialysis machine includes a first pump motor 227 for coupling with the disposable cartridge's first pump actuator 51, a second pump motor 221 for coupling with the disposable cartridge's second pump actuator 53, and a third pump motor 231 for coupling with the disposable cartridge's third pump actuator 55. Preferably, the pump motors are traditional commercial off-the-shelf electric rotary motors as can be selected by those skilled in the art.

As illustrated in FIG. 6, preferably each pump actuator (51, 53 and 55) does not employ deformable members for providing pumping action, such as employed with a common roller pump engaging an arterial line or venous line. Instead, the preferred pump actuators possess a sliding vane construction. To this end, each pump actuator includes an inlet 57 for introducing fluid into a cavity 63 and an outlet 59 for expelling such fluids. Furthermore, each pump actuator includes a circular rotor 65 having slots 67 for receiving radially moving vanes 69. Centrifugal force, hydraulic pressure and/or a biasing means, such as springs or push rods, push the vanes to the walls of the cavity 63 to form chambers formed by the rotor, vanes and cavity sidewall. In the preferred embodiment illustrated in FIG. 6, centrifugal force caused by rotation of the rotor pushes the vanes to the cavity sidewall. Preferably, the cavity 63 and rotor 67 are substantially circular and the rotor is positioned within the larger cavity. However, the rotor's center and cavity's center are axially offset (eccentric) from one another. In operation, the rotor 65 and vanes 69 form an impeller. As the rotor rotates, fluid enters the pump actuator through the inlet 57. Rotation of the rotor and vanes pump fluid to be propelled from the pump actuator's outlet 59. Preferably, each pump actuator is made of substantially non-deformable materials including Federal Drug Administration approved plastics. As used herein, the term "non-deformable" is not meant to mean that the pump actuator components will not undergo some insignificant deformation during pump operation. However, the non-deformable pump actuator components do not deform in a manner to provide pumping action such as provided by a peristaltic roller pump engaging a flexible tube, such as a blood line, as is commonly employed for current hemodialysis treatment. In the preferred embodiments, the pump actuator's housing and rotor are made of polycarbonate, and the pump actuator's vanes are made of polyether ether ketone (PEEK).

Still with reference to FIG. 6, the pump actuator's rotor 63 may be connected to the electric motor 67 by various constructions known to those skilled in the art. For example, the rotor may include a shaft which is keyed to form a press fit with a corresponding receptacle formed in the rotor. However, in the preferred embodiment illustrated in FIG. 6, the motor 227 and rotor 65 are coupled utilizing magnets 71. As illustrated, a preferred rotor possesses six magnets wherein the polarity (north-south direction) is alternated for each adjacent magnet 71. Similarly, the motor 227 contains six additional magnets 71 wherein the polarity of each magnet is alternated. When a disposable cartridge 11 is coupled to the dialysis machine 201, the motor magnets are positioned and aligned to come in close contact with the rotor magnets. Magnetic forces couple the pump motors to the pump actuators so that controlled activation of the pump motors rotates the rotors, and thus operates the pump actuators.

Figure 12:
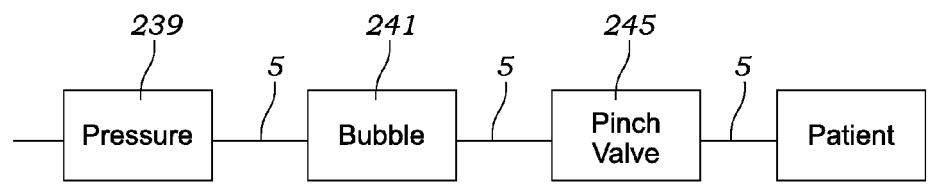
FIG. 12 is a flow chart illustrating a safety feature of the hemodialysis system including pressure sensor, bubble sensor and pinch valve, in accordance with at least one embodiment.

As discussed in detail below, in addition to the sensors found in the disposable cartridge 11, the preferred dialysis machine 201 also possesses various sensors for monitoring proper operation of the hemodialysis system 1. For example, the dialysis machine preferably includes a temperature sensor 223 for measuring the temperature of the dialysis within the reservoir 209. In addition, the dialysis system includes an ammonia sensor 237 (see FIG. 15) which is positioned adjacent to the filter's vapor membrane 87 for detecting any ammonia within the filter 79. As illustrated in FIGS. 2, 3 and 12, preferably the dialysis machine 201 also includes a pair of sensors (239 and 241) and a valve 245 connected to the venous blood line 5 for providing still additional redundant safety to a patient. The additional sensors include a pressure sensor 239 for measuring the pressure of the blood in the venous blood line 5 and a bubble sensor 241 to determine whether there are any unwanted air bubbles in the venous blood line 5. In the event that the blood pressure is not within a predetermined range or in the event that an unwanted air bubble is detected, a pinch valve 245 is made to close.

Figure 14:
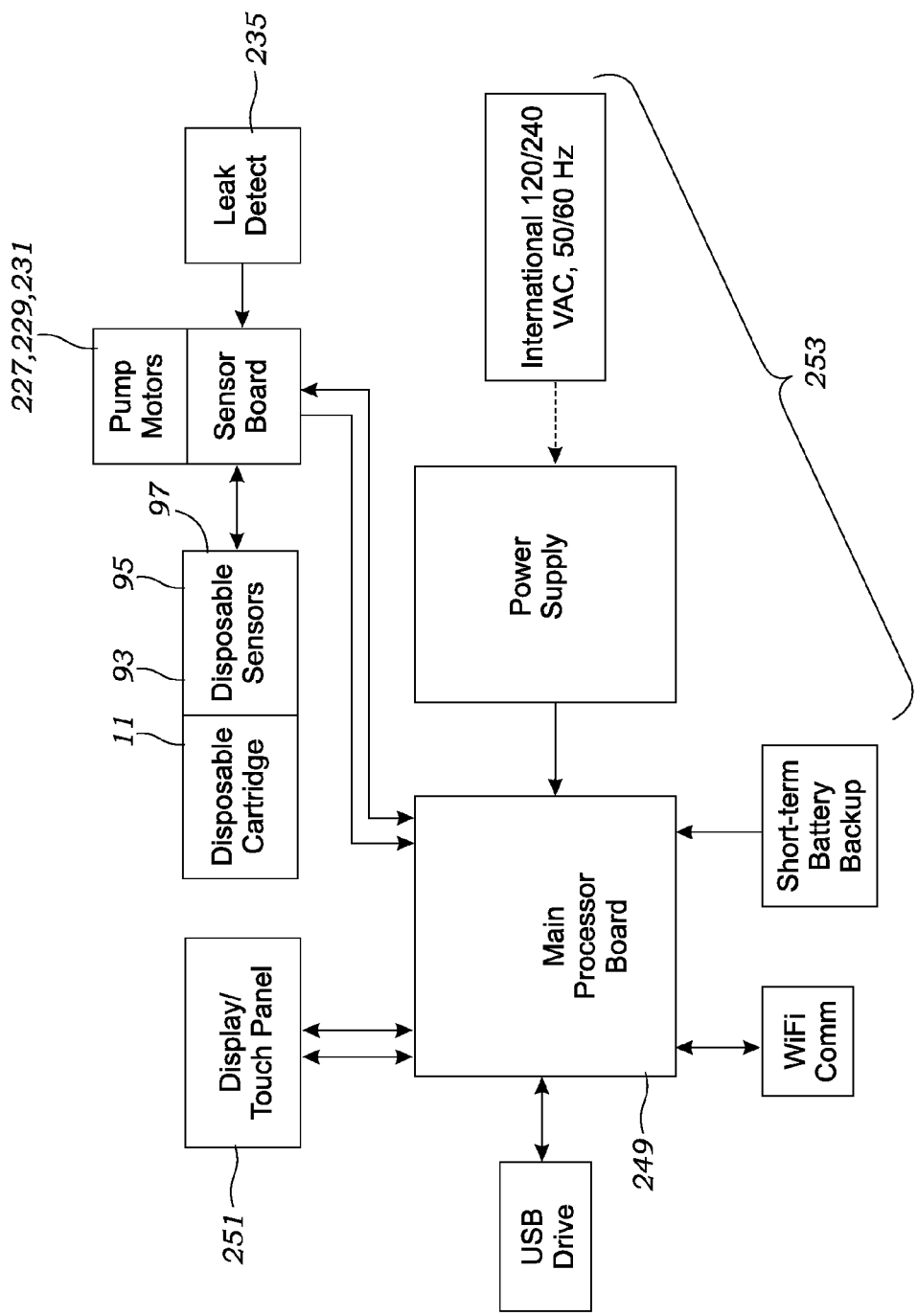
FIG. 14 is a diagram illustrating the connection of the various electronics and electromechanical components of the hemodialysis system, in accordance with at least one embodiment.

With reference to FIG. 14, the dialysis machine 201 includes a processor 249, a user interface 25, and a power supply 253 for providing power to the processor 249, user interface 251, pump motors, and sensors. The processor 249 is connected to the dialysis machine sensors (including reservoir level sensor 217, blood leak sensor 235, ammonia sensor 237, venous blood line pressure sensor 239, and venous blood line bubble sensor 241), three pump motors 227, 229 and 231, and pinch valve 245 by traditional electrical circuitry. In addition, the dialysis machine possesses electrical terminals 247 (see FIG. 11) for connecting to the disposable cartridge's electrical terminals 101 so as to connect the processor 249 with the disposable cartridge's sensors (including flow and pressure sensors). The processor may be a general purpose computer or microprocessor including hardware and software as can be determined by those skilled in the art to monitor the various sensors and provide automated or directed control of the heater, pumps, and pinch valve. The processor may be located within the electronics of a circuit board or within the aggregate processing of multiple circuit boards.

In operation, the processor 249 is electrically connected to the first, second and third pump motors for controlling the activation and rotational velocity of the pump motors, which in turn controls the pump actuators, which in turn controls the pressure and fluid velocity of blood through the blood flow path and dialysate through the dialysate flow path. By independently controlling operation of the first and second pump actuators, the processor can maintain, increase or decrease the pressure and/or fluid flow within the dialysate flow path within the dialyzer. Moreover, by controlling all three pump actuators independently, the processor 249 can control the pressure differential across the dialyzer's semipermeable membrane to maintain a predetermined pressure differential (zero, positive or negative), or maintain a predetermined pressure range. For example, most hemodialysis is performed with a zero or near zero pressure differential across the semipermeable membrane, and to this end, the processor can monitor and control the pumps to maintain this desired zero or near zero pressure differential. Alternatively, the processor may monitor the pressure sensors and control the pump motors, and in turn pump actuators, to increase and maintain positive pressure in the blood flow path within the dialyzer relative to the pressure of the dialysate flow path within the dialyzer. Advantageously, this pressure differential can be affected by the processor to provide ultrafiltration and the transfer of free water and dissolved solutes from the blood to the dialysate.

Moreover, the processor monitors all of the various sensors to ensure that the hemodialysis machine is operating efficiently and safely, and in the event that an unsafe or non-specified condition is detected, the processor corrects the deficiency or ceases further hemodialysis treatment. For example, if the venous blood line pressure sensor 239 indicates an unsafe pressure or the bubble sensor 241 detects a gaseous bubble in the venous blood line, the processor signals an alarm, the pumps are deactivated, and the pinch valve 245 is closed to prevent further blood flow back to the patient. Similarly, if the blood leak sensor 235 detects that blood has permeated the dialyzer's semipermeable membrane, the processor 249 signals an alarm and ceases further hemodialysis treatment.

The dialysis machine's user interface 251 may include a keyboard or touch screen for enabling a patient or medical personnel to input commands concerning treatment or enable a patient or medical personnel to monitor performance of the hemodialysis system. Moreover, the processor may include Wi-Fi connectivity for the transfer of information or control to a remote location.

As mentioned above, the hemodialysis system 1 incorporates numerous improved sensors never before incorporated into a hemodialysis device. The improved sensors include ammonia sensor 237, fluid level sensor 217, and blood leak sensor 235. Each of these sensors is described in greater detail below.

Ammonia Sensor System

As also mentioned above, the at least one ammonia sensor 237 is positioned adjacent to the filter's vapor membrane 87 and configured for detecting any ammonia within the filter 79. In a bit more detail, in at least one embodiment, each ammonia sensor 237 incorporates a heater (not shown) having the following parameters:

| Parameter | Symbol | Min | Typ | Max | Unit |
| --- | --- | --- | --- | --- | --- |
| Heating Power | $P_H$ | 60 | 66 | 73 | mW |
| Heating Voltage | $V_H$ | | 2.2 | | V |
| Heating Current | $I_H$ | | 30 | | mA |
| Heating Resistance at Nominal Power | $R_H$ | 64 | 72 | 80 | Ω |

In at least one embodiment, due to the nature of the chemo-sensitive film on the ammonia sensor 237, it is important that the temperature rise from the heater be repeatable and consistent over the lifetime of the ammonia sensor 237. To that end, it is also important to control the power applied to the heater as consistently as possible, especially knowing the resistance of the heater changes over the lifetime of the ammonia sensor 237. In at least one embodiment, the ammonia sensor 237 uses a single load resistor in series with the heater. This configuration is extremely sensitive to variations in VCC as well as $R_H$. Using nominal VCC=3.3V±3.0% and $R_L$=36.5Ω±1.0% produces $P_H$=0.0669 W±10.3% (with design center $P_H$=0.0667 W) as demonstrated in the following table:

| $V_{cc}$ (V) | $R_H$ (ohm) | $R_L$ (OHM) | $P_H$ (W) |
| --- | --- | --- | --- |
| 3.201 | 64 | 36.135 | 0.0654 |
| 3.201 | 64 | 36.865 | 0.0645 |
| 3.201 | 80 | 36.135 | 0.0608 |
| 3.201 | 80 | 36.865 | 0.0600 |
| 3.399 | 64 | 36.135 | 0.0737 |
| 3.399 | 64 | 36.865 | 0.0727 |

-continued

| $V_{cc}$ (V) | $R_H$ (ohm) | $R_L$ (OHM) | $P_H$ (W) | |
|---|---|---|---|---|
| 3.399 | 80 | 36.135 | 0.0685 | |
| 3.399 | 80 | 36.865 | 0.0677 | |
| | | Min | 0.0600 | −10.3% |
| | | Max | 0.0737 | 10.3% |

Figure 16:
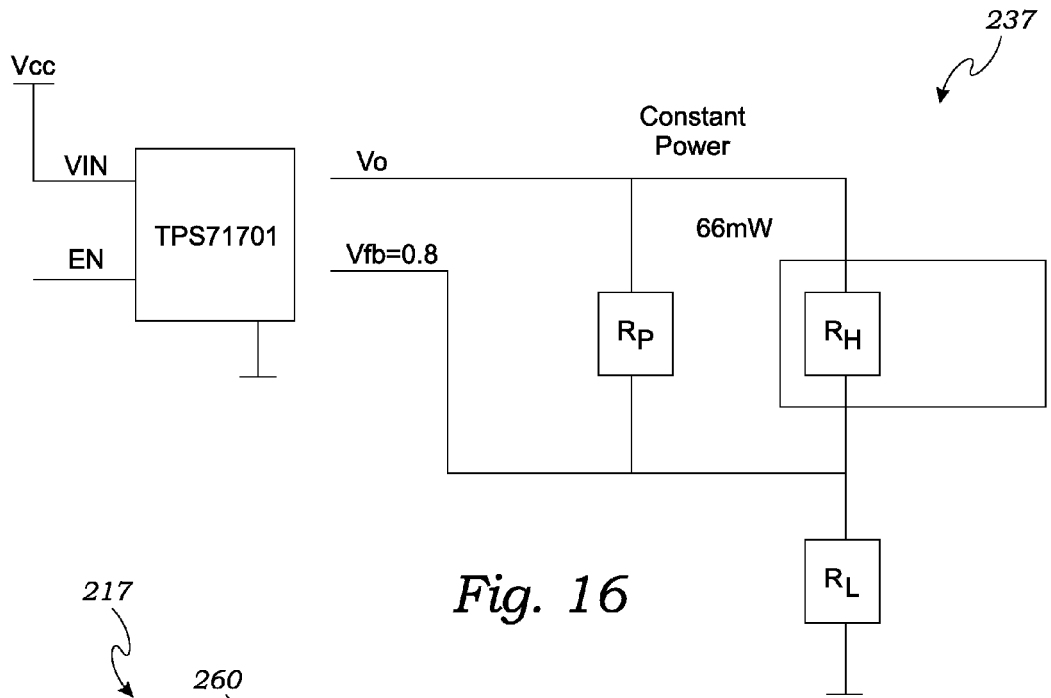
FIG. 16 is a circuit diagram of an exemplary heater of an ammonia sensor, in accordance with at least one embodiment.

In at least one embodiment, in order to more tightly control the power dissipation in the heater, the circuit shown in FIG. 16 is used. The LDO is used to force a constant current through $R_L$, and $R_P$ is used to balance the current through $R_H$. Using $V_{FB}$=0.8V±1.25%, $R_L$=13.0Ω±1%, $R_P$=69.8Ω±1%, $P_H$=0.0658 W±1.65% (with design center $P_H$=0.0661 W) as demonstrated in the following table:

| $V_{FB}$ (V) | $R_L$ (OHM) | $R_H$ (ohm) | $R_P$ (ohm) | $P_H$ (W) | |
|---|---|---|---|---|---|
| 0.79 | 12.87 | 64 | 69.102 | 0.0650 | |
| 0.79 | 12.87 | 64 | 70.498 | 0.0663 | |
| 0.79 | 12.87 | 80 | 69.102 | 0.0647 | |
| 0.79 | 12.87 | 80 | 70.498 | 0.0661 | |
| 0.79 | 12.87 | 64 | 69.102 | 0.0650 | |
| 0.79 | 12.87 | 64 | 70.498 | 0.0663 | |
| 0.79 | 12.87 | 80 | 69.102 | 0.0647 | |
| 0.79 | 12.87 | 80 | 70.498 | 0.0661 | |
| 0.81 | 13.13 | 64 | 69.102 | 0.0656 | |
| 0.81 | 13.13 | 64 | 70.498 | 0.0669 | |
| 0.81 | 13.13 | 80 | 69.102 | 0.0654 | |
| 0.81 | 13.13 | 80 | 70.498 | 0.0668 | |
| 0.81 | 13.13 | 64 | 69.102 | 0.0656 | |
| 0.81 | 13.13 | 64 | 70.498 | 0.0669 | |
| 0.81 | 13.13 | 80 | 69.102 | 0.0654 | |
| 0.81 | 13.13 | 80 | 70.498 | 0.0668 | |
| | | | Min | 0.0647 | −1.65% |
| | | | Max | 0.0669 | 1.65% |

The maximum power dissipation is $P(R_L)$=0.050 W and P(RP)=0.076 W, which are well within normal operating parameters of 1/10 W, 0603 resistors. The maximum VOUT required by the LDO is 3.12 V ($V(R_H)$+$V_{FB}$). The dropout voltage at 62 mA is ~80 mV. $V_{CC}$(min)=3.12+0.08=3.20 V, which requires a VCC supply of 3.3V±3%.

In at least one embodiment, the sensitive layer of the ammonia sensor 237 has chemo resistive characteristics. Due to the fabrication of the sensitive layer, the reference resistance, $R_0$ (ambient conditions, synthetic air), is unable to be tightly controlled. Gas sensing is performed by taking the current sensing resistance, $R_S$, and dividing it by the ambient resistance, as the $SnO_2$ gas sensing layer reduces the $NH_3$ (as well as other gasses) at high temperatures, under bias and conductivity increases. The $R_S$/$R_0$ ratio is indicative of the gas concentration, and is used for calibration and threshold detection. The sensitive layer characteristics are shown in the table below:

| Characteristic | Symbol | Min | Max | Unit |
|---|---|---|---|---|
| Sensing resistance in air | $R_0$ | 10 | 1,500 | KΩ |
| Sensitivity Factor (1 ppm $NH_3$) | $S_R$ | 1.5 | 15 | |
| $R_0$/$R_S$ Ratio (1 ppm $NH_3$) | $R_S$/$R_0$ | 0.67 | 0.067 | |
| Minimum $R_S$ | $R_S$ | 820 | | |
| Sensitive Layer Power Dissipation | $P_S$ | | 8 | mW |

Since the output of the ammonia sensor 237 will be read across $R_L$ (differential), $V(R_L)$ must be kept below differential full scale input range of the converter (0.5V) for proper in-limits conversion. Due to the wide dynamic range of $R_0$, it is apparent that multiple resistances need to be switched in order to manage the readout of the ammonia sensor 237. The following illustrates the configuration of at least one embodiment. With the low currents involved, the GPIO signals can be assumed to be GND (or repeatably close to GND). The GPIO pin is either left in the High-Z condition (floating), or driven 0.

| GPIO 1 | GPIO 0 | $R_L$ (effective) | $R_S$ (min) | $V_L$ ($V_S$=10K) | $V_L$ ($V_S$=100K) | $V_L$ ($V_S$=1M) | $V_L$ ($V_S$=1.5M) |
|---|---|---|---|---|---|---|---|
| 0 | 0 | 200 | 800 | 49 mV | 5 mV | 500 μV | 333 μV |
| 0 | Z | 2.2K | 8.8K | 450 mV | 54 mV | 5.5 mV | 3.7 mV |
| Z | Z | 22.2K | 89K | -over- | 450 mV | 54 mV | 36 mV |

This configuration is used to ensure the highest voltage practical across the sensitive layer in order to ensure proper reduction at the sensitive layer gain boundaries. The maximum current and power through the sensitive layer is defined by the following formula:

$$I_S = \frac{2.5}{R_S + R_L} = \frac{2.5}{820 + 200} = 2.5 \, \text{mA}$$

$$P_S = I_S^2 * R_S = 0.0025^2 * 820 = 5.1 \, \text{mW}$$

It should also be noted that the internal gain of the converter can be used to increase the dynamic range once the baseline $R_0$ is determined after warm-up.

Blood Leak Sensor

As also mentioned above, the blood leak sensor 235 is positioned and configured for detecting whether blood has permeated the semipermeable membrane of the dialyzer 25. In a bit more detail, in at least one embodiment, the blood leak sensor 235 uses the principle of optical absorption to determine the presence of blood in the dialysate. Using two separate wavelength emitters, the blood leak sensor 235 compensates for changes in the dialysate clarity.

Level Sensor

Figure 13:
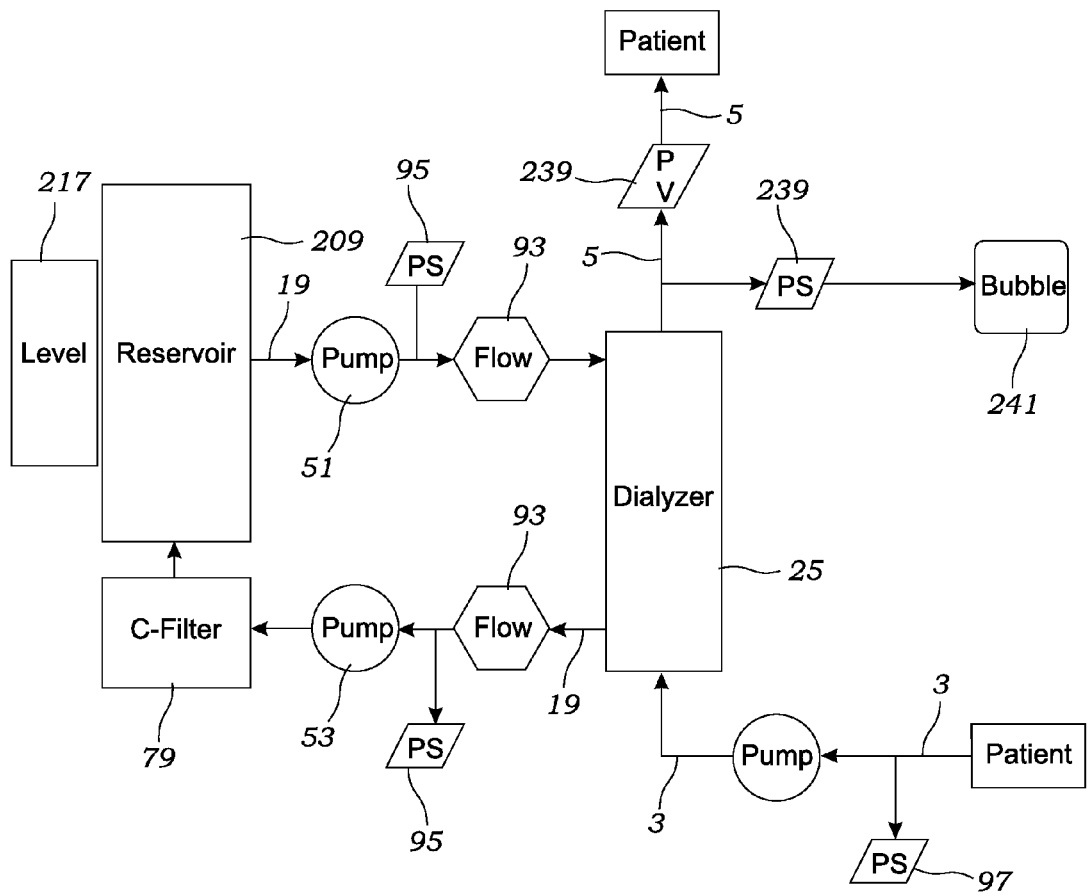
FIG. 13 is a flow chart illustrating the flow of blood and dialysate through the hemodialysis system, in accordance with at least one embodiment.
Figure 15:
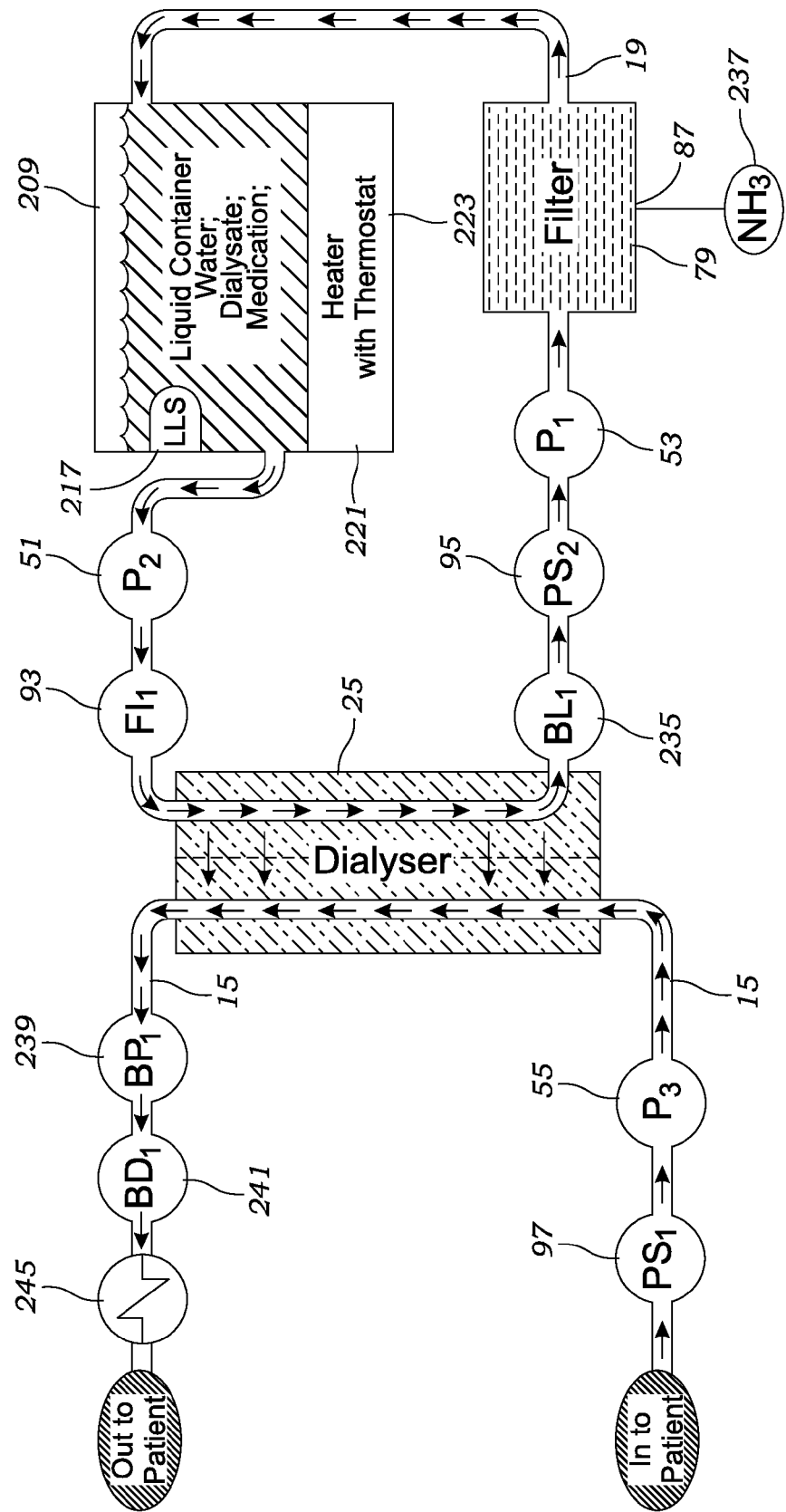
FIG. 15 is a more detailed flow chart illustrating the flow of blood and dialysate through the hemodialysis system, in accordance with at least one embodiment.

As also mentioned above, the at least one level sensor 217 is positioned and configured for monitoring and measuring the level of the dialysate fluid in the dialysate reservoir 209 (FIGS. 13 and 15). In at least one embodiment, the fluid is contained within the reservoir 209, and the level sensor 217 is positioned outside and adjacent the reservoir 209. The level sensor 217 provides a safety critical function as it monitors the dialysate reservoir 209 for increases and decreases in fluid level. Aside from catastrophic fluid loss (i.e., ruptured reservoir 209 or flow path 19), gain or loss of dialysate fluid indicates the pressure balance across the dialyzer 25 is incorrect and must be adjusted.

Figure 17:
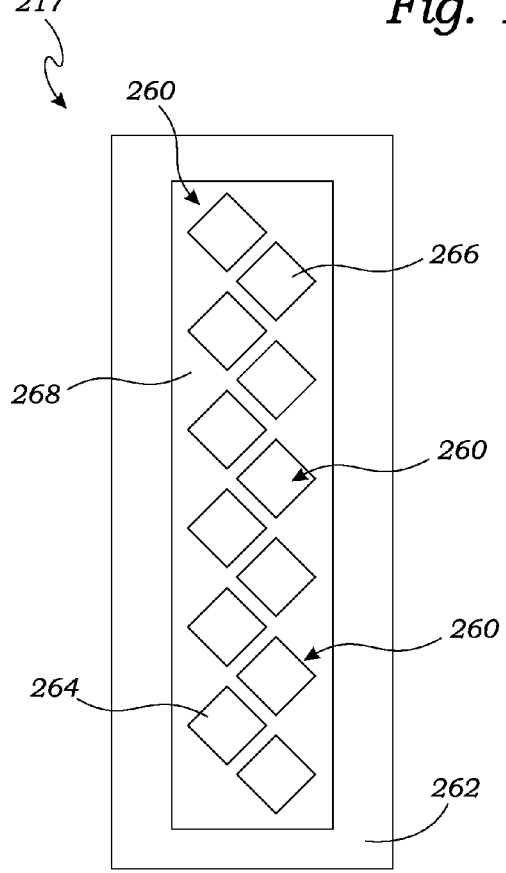
FIG. 17 is a diagram illustrating the arrangement of electrodes provided by an exemplary level sensor, in accordance with at least one embodiment.

In a bit more detail, in at least one embodiment, the level sensor 217 uses change in capacitance to determine the fluid level in the reservoir 209. A series of electrodes 260 and a ground surface 262 are positioned adjacent to the reservoir 209, and the change in capacitance at a given electrode 260 reflects the presence or absence of the mildly conductive dialysate fluid. In at least one embodiment, as illustrated in FIG. 17, the electrodes 260 are arranged in a staggered pattern, providing overlap between electrodes 260. This overlap also allows for relatively better level resolution than non-overlapped electrodes 260. The capacitive coupling between the electrodes 260 and ground surface 262 ("GND") changes depending on the presence of the dialysate fluid. This change in capacitance is measured and used to determine the fluid level across all electrodes 260. Among the electrodes 260, the level sensor 217 includes a wet reference electrode 264 and a dry reference electrode 266, which are used as references for the capacitive coupling of the dialysate fluid, and the ambient capacitive coupling. In at least one embodiment, the wet reference electrode 264 is positioned for always being below the dialysate fluid level, and the dry reference electrode 266 is positioned for always being above the dialysate fluid level during normal operation.

With continued reference to FIG. 17, in at least one embodiment, the level sensor 217 further provides a capacitance-to-digital converter (not shown), which measures the capacitance between each of the electrodes 260 and ground surface 262. The level sensor 217 also provides an AC shield output 268, which is in-phase with the driven electrode 260, and is used to isolate the electrode 260 from stray ground coupling. The AC shield 268 is used in a plane behind the electrodes 260 to shield the electrodes 260 from stray ground, and in an electrode position to assure equal loading for each of the electrodes 260. In at least one embodiment, each electrode 260 is a symmetric square rotated ninety degrees, with an overall height of 12 mm and an overall width of 12 mm (a rotated square with all sides of 8.49 mm long) with an area of 72 mm². The electrodes 260 are spaced vertically at 7.5 mm between electrode 260 centers. The volume of dialysate fluid represented by this space is proportional to the cross-section area at the fluid level. In the exemplary embodiment, the cross-sectional area of the reservoir 209 is 3.102 mm². The volume represented by a deviation in level is calculated using the following equation:

$$Vol(ml) = \frac{3{,}102 \text{ mm}^2 * \text{deviation (mm)}}{1000 \frac{\text{mm}^3}{\text{ml}}}$$

In the exemplary embodiment, the level sensor 217 has a basic span (±18.75 mm) of ±58 ml, which represents 5.8% of the dialysate fluid.

In closing, regarding the exemplary embodiments of the present invention as shown and described herein, it will be appreciated that a portable hemodialysis machine and disposable cartridge is disclosed. Because the principles of the invention may be practiced in a number of configurations beyond those shown and described, it is to be understood that the invention is not in any way limited by the exemplary embodiments, but is generally directed to a portable hemodialysis machine and disposable cartridge and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

While several particular forms of the invention have been illustrated and described, it will be apparent that various modifications can be made without departing from the spirit and scope of the invention. Therefore, it is not intended that the invention be limited except by the following claims.

What is claimed is:

1. A hemodialysis system comprising:
   an arterial blood line for connecting to a patient's artery for collecting blood from a patient;
   a venous blood line for connecting to a patient's vein for returning blood to a patient;
   a dialyzer;
   a blood flow path connected to said arterial blood line and said venous blood line for transporting blood from a patient to said dialyzer and back to a patient;
   a reservoir for storing a dialysate solution;
   a dialysate flow path, isolated from the blood flow path, for transporting a dialysate from said reservoir to said dialyzer and back to said reservoir;
   a filter connected to said dialysate flow path downflow from said dialyzer for removing uremic toxins from dialysate in said a dialysate flow path after said dialyzer and prior to returning said dialysate to said reservoir;
   a first pump including a first pump motor and a first pump actuator connected to said dialysate flow path upflow from said dialyzer for pumping dialysate through said dialysate flow path to said dialyzer, said first pump actuator including a sliding vane construction having non-deformable components including a housing having a central cavity forming an internal sidewall, a rotor eccentrically positioned within said cavity and said rotor having a plurality of radially aligned slots at said rotor's periphery, vanes slideably positioned in said slots to slide in and out of said slots so as to seal with the cavity's internal sidewall creating vane chambers that pump dialysate through said dialysate flow path;
   a second pump including a second pump motor and a second pump actuator connected to said dialysate flow path upflow from said dialyzer for pumping dialysate through said dialysate flow path, said second pump actuator including a sliding vane construction having non-deformable components including a housing having a central cavity forming an internal sidewall, a rotor eccentrically positioned within said cavity and said rotor having a plurality of radially aligned slots at said rotor's periphery, vanes slideably positioned in said slots to slide in and out of said slots so as to seal with the cavity's internal sidewall creating vane chambers that pump dialysate through said dialysate flow path; and
   a third pump including a third pump motor and a third pump actuator connected to said blood flow path for pumping blood through said blood flow path, said third pump actuator including a sliding vane construction having non-deformable components including a housing having a central cavity forming an internal sidewall, a rotor eccentrically positioned within said cavity and said rotor having a plurality of radially aligned slots at said rotor's periphery, vanes slideably positioned in said slots to slide in and out of said slots so as to seal with the cavity's internal sidewall creating vane chambers that pump blood through said blood flow path; and
   a processor connected to said first, second and third pump motors for controlling operation of said pump motors.

2. The hemodialysis system of claim 1 further comprising:
   a reusable dialysis machine and a disposable cartridge wherein said disposable cartridge is connectable and disconnectable to said reusable dialysis machine; and
   said first, second and third pump motors are positioned with said reusable dialysis machine and said first, second and third pump actuators are positioned with said disposable cartridge.

3. The hemodialysis system of claim 1 wherein dialyzer includes a semipermeable membrane that separates said blood flow path and said dialysate flow path and said processor monitors said pressure sensors and controls said pump motors so as to maintain a predetermined pressure differential across said semipermeable membrane.

4. The hemodialysis system of claim 3 wherein said processor maintains said pressure differential within the dialyzer of the blood flow path relative to dialysate flow path at about zero.

5. The hemodialysis system of claim 3 wherein said processor maintains said pressure differential within the dialyzer of the blood flow path relative to dialysate flow path above zero to provide ultrafiltration.

6. The hemodialysis system of claim 1 wherein said first, second and third pump motors are electric rotary motors.

* * * * *